United States Patent [19]

Burkinshaw et al.

[11] Patent Number: 5,021,055
[45] Date of Patent: Jun. 4, 1991

[54] PATELLAR CLAMP AND SURGICAL SAW GUIDE

[75] Inventors: Brian D. Burkinshaw; Steven G. Brown, both of Pflugerville, Tex.

[73] Assignee: Intermedics Orthopedics, Inc., Austin, Tex.

[21] Appl. No.: 585,315

[22] Filed: Sep. 19, 1990

[51] Int. Cl.⁵ .............................. A61F 5/00
[52] U.S. Cl. ........................... 606/82; 606/88; 606/87
[58] Field of Search ............ 606/82, 87, 88, 79, 606/102

[56] References Cited

U.S. PATENT DOCUMENTS

| | | | |
|---|---|---|---|
| 4,633,862 | 1/1987 | Peterson | 606/82 |
| 4,703,751 | 11/1987 | Pohl | 606/87 |
| 4,759,350 | 7/1988 | Dunn et al. | 606/82 |
| 4,892,093 | 1/1990 | Zarnowski et al. | 606/82 |
| 4,893,619 | 1/1990 | Dale et al. | 606/87 |
| 4,952,213 | 8/1990 | Bowman et al. | 606/79 |
| 4,952,214 | 8/1990 | Comparetto | 606/87 |

*Primary Examiner*—Stephen C. Pellegrino
*Assistant Examiner*—Gary Jackson
*Attorney, Agent, or Firm*—John R. Merkling

[57] ABSTRACT

A patellar clamp and saw guide for preparing a patella to receive a prosthetic articulating surface on the patella's posterior side. A guide plate supports a saw block. The guide plate can be swiveled so that a sagittal saw can be presented to the patella from any desired angle. The saw block can be advanced or retracted axially so that more or less of the patella will be cut away by the saggittal saw. A scale enables the location of the proposed cut to be quickly and accurately determined. Storage apparatus in a handle of the clamp holds different specialized for use during surgery.

12 Claims, 3 Drawing Sheets

PATELLAR CLAMP AND SURGICAL SAW GUIDE

BACKGROUND OF THE INVENTION

Our invention relates to orthopedic surgical guides and jigs. Specifically our invention is a clamp and saw guide for holding a human patella and providing a guide so that a predetermined portion of the patella may be accurately removed by sawing.

The two largest and longest bones of the human body, the femur and tibia, meet at a person's knee. The tibia is situated at the front and inner side of the lower leg. It is prismoid in form, and expanded above where it enters into the knee joint. The head of the tibia is large and expanded on each side into two eminences, the condyles. These eminences form two smooth concave compartments or surfaces which articulate with the condyles of the femur. The medial condyle is more prominent anteriorly and broader both in the anterior-posterior and transverse diameters than the lateral condyle. Accordingly, the lateral articular surface of the tibia is shorter, more shallow and narrower than the medial surface of the tibia. The medial surface is broader, more circular, and concave from side to side. The anterior surfaces of the tuberosities are continuous with one another, forming a single large surface which is somewhat flattened. Posteriorly the tuberosities are separated from each other by a shallow depression for attachment of ligaments. The medial tuberosity presents posteriorly a deep transverse groove for the insertion of a tendon.

The patella is a seasamoid or lens shaped bone which slides in a groove between the condyles of the femur. Its function is to increase the efficiency of the quadriceps muscle by shifting the line of action of the muscle's pull forward. As the knee articulates, the muscles and tendons force the patella toward the condyles of the femur. Consequently, there is considerable relative motion between the patella and the other bones comprising the knee joint.

Because of aging or disease, the articulating surfaces of the knee may degrade. To treat certain pathologies, it has become common to surgically remove the condyles and replace these structures with prosthetic implants. By the same processes, the articulating surfaces of the patella may also degrade. In connection with the implantation of a prosthetic knee, therefore, the articulating surface of the patella may also be replaced. Because of the tendons connected to the patella, it is generally advisable to replace only the articulating surface. An ultra high molecular weight polyethylene articulating surface, with or without a metal baseplate, will be implanted on the posterior side of the patella, adjacent the femoral condyles. To implant such a prosthesis, the posterior surface of the patella is resected to produce a flat surface upon which the prosthesis can be mounted. In the past, the surgeon has often relied on skill of hand and eye in manipulating a sagittal saw to make an appropriate cut.

SUMMARY OF MY INVENTION

We have invented a patellar clamp and saw guide for use by a surgeon in preparing a patella to receive a prosthetic articulating surface on the patella's posterior side. The clamp and saw guide, according to my invention, captures a patella between a base and a cap. A guide plate is provided which supports a saw block. The guide plate can be swiveled around the base so that a sagittal saw can be presented to the patella from any desired angle. When the desired rotational angle has been found, the guide plate can be secured in the selected position. Then the saw block can be advanced or retracted axially so that more or less of the patella will be cut away by the sagittal saw. We have provided a scale mounted on the cap which enables the vertical location of the proposed cut to be quickly and accurately determined. Consequently, the amount of bone removed from the patella can correspond precisely to optimal dimensions for the anatomy encountered and for the prosthesis being used by the surgeon. We have also provided storage apparatus in a handle of the clamp so that different specialized caps can be stored and can be available for use during surgery.

In view of the foregoing, it is an object of our invention to provide a patellar clamp and saw guide which will enable a surgeon to accurately resect a selected amount of bone from a patella.

It is a further object of our invention to provide such a clamp and saw guide with means for accurately measuring the amount of bone to be removed.

It is a further object of our invention to provide a patellar clamp and saw guide which can be used on either the right or the left knee.

Another object of our invention is to provide a patellar saw guide with a quick storage feature to hold interchangeable parts which may be needed for particular conditions during surgery.

These and other objects of our invention will be apparent from the following detailed description taken with reference to the accompanying drawings.

DETAILED DESCRIPTION OF OUR PREFERRED EMBODIMENT

Figure 1:
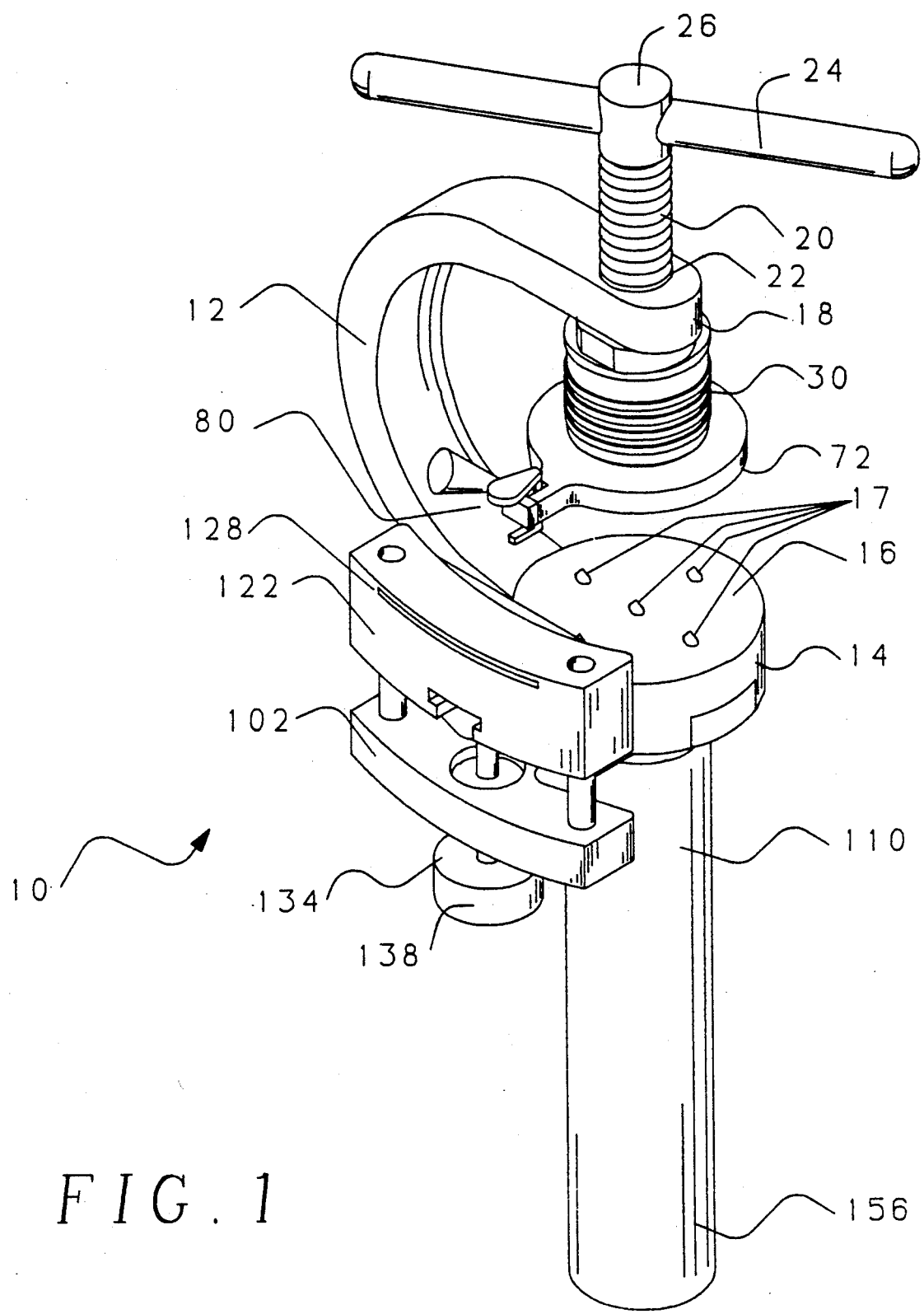
FIG. 1 is a perspective view of patellar clamp and saw guide according to our present invention.

We will now describe our prefered embodiment of our invention by reference to the accompanying drawings. Like numerals will refer to like parts in each drawing. FIG. 1 is a perspective view of a patellar clamp and saw guide 10 according to our present invention. The clamp 10 comprises a bracket 12 which supports a base 14. In using clamp 10, a surgeon would lay a patient's patella on a upper surface 16 of the base 14. In our preferred embodiment, the upper surface 16 is slightly concave to conform generally to the expected convex shape of the patella. Pins 17 may protrude from the upper surface 16 to resist movement of the patella. The bracket 12 is curved into a C-shape. At an upper end 18 thereof, over the base 14, a bolt 20 is screwed through a threaded bore 22. A "T" handle 24 is provided on a proximal end 26 of the bolt 20 so that adequate torque can be imparted to the bolt.

Figure 2:
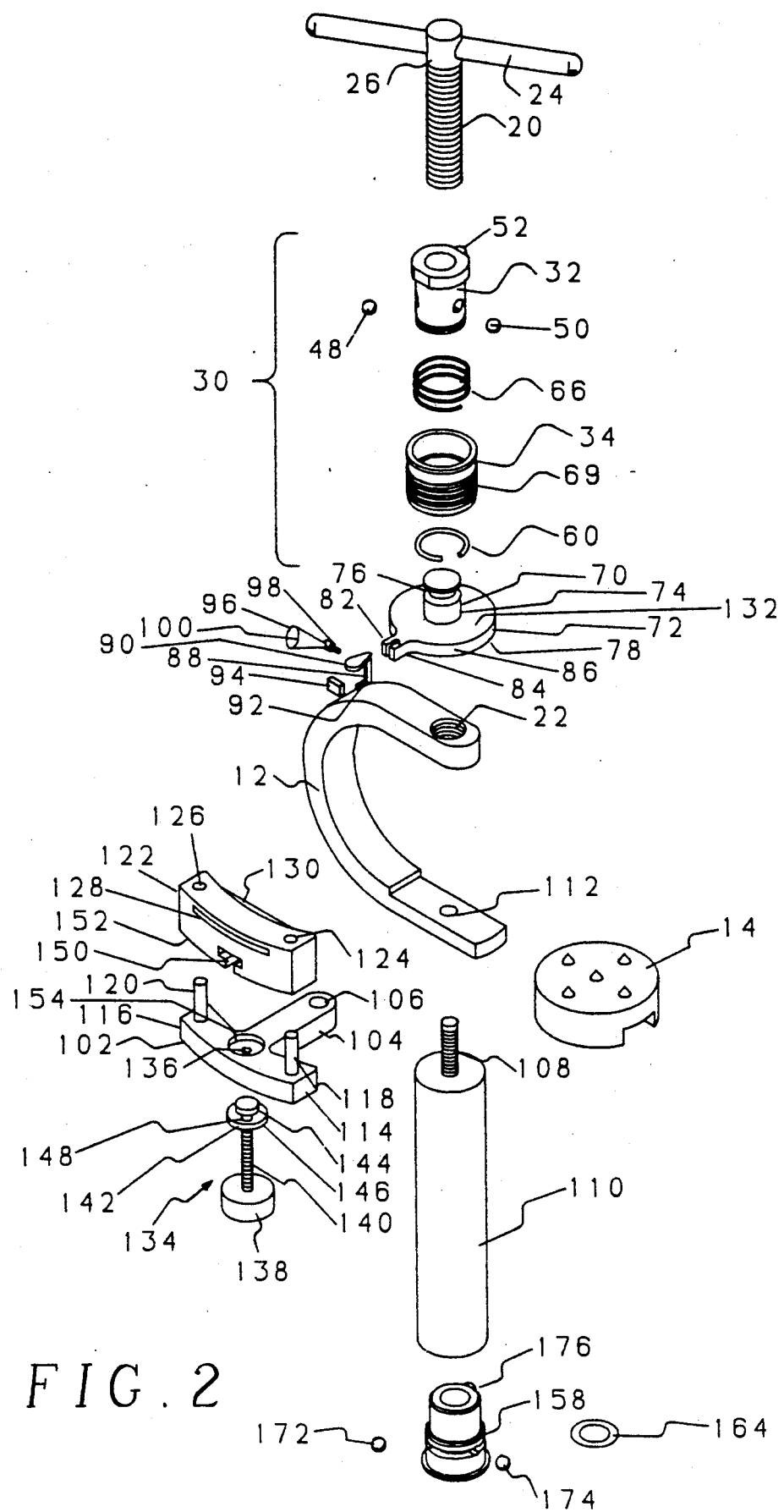
FIG. 2 is an exploded perspective view of the patelar clamp and saw guide of FIG. 1.
Figures 3, 4:
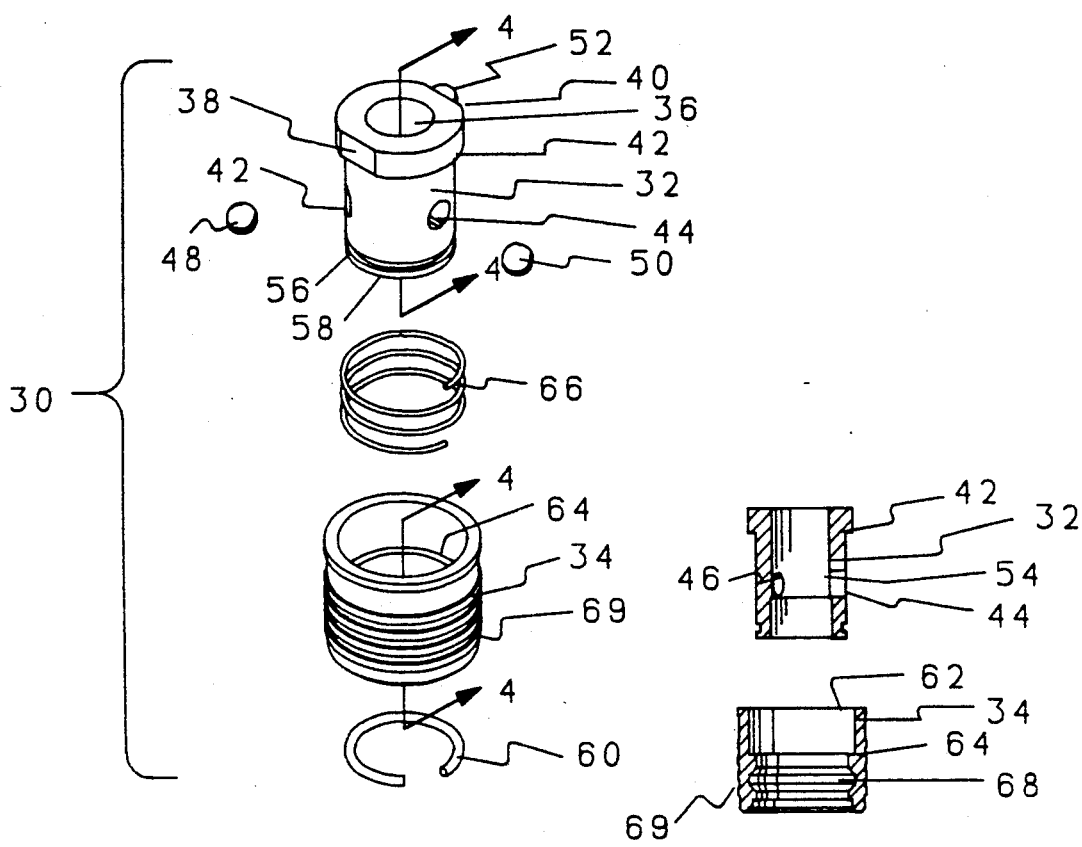
FIG. 3 is an enlarged, exploded perspective view of a conector for use with the clamp of FIG. 1.
FIG. 4 is a through section of portions of the connector of FIG. 3 taken along line 4—4.
Figures 5, 6:
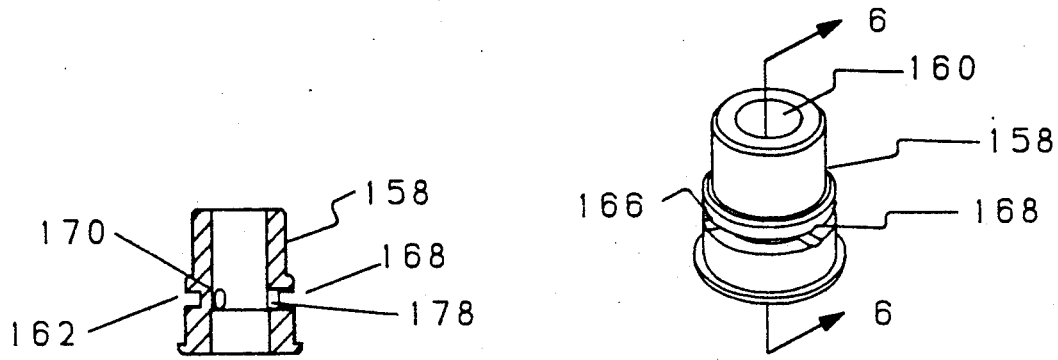
FIG. 5 is a perspective view of a storage apparatus for additional caps for use in the clamp of FIG. 1.
FIG. 6 is a through section of the storage apparatus of FIG. 5 taken along line 6—6.

At a distal end 28 of the bolt 20 there is connector nut 30. The connector 30 is comprised of an inner sleeve 32 and an outer sleeve 34, as shown in FIGS. 2 and 3. The inner sleeve 32 has an upper threaded bore 36 for attachment to the bolt 20. Wrench flats 38, 40 are provided on a upper lip 42 for tightening the inner sleeve 32 to the bolt 20. Three axial bores, 42, 44, 46 are provided to receive balls 48, 50, 52 respectively. At an inner end of each bore 42, 44, 46 a lip 54 is provided to prevent the balls 48, 50, 52 from falling into the interior of the sleeve 32. A groove 56 is provided at a bottom end 58 of the inner sleeve 32 for receiving a split ring 60. The outer ring 34 has an upper bore 62 which terminates in a lip 64. When the outer sleeve 34 is placed over the inner sleeve 32, a sping 66 is captured between the lip 42 on the inner sleeve and the lip 64 on the outer sleeve. The spring 66 forces the outer sleeve 34 downward and, as will be explained below, presses the balls 48, 50, 52 inwardly through the bores 42, 44, 46.

Below the lip 64 in the outer sleeve 34, there is a groove 68. When the outer sleeve 34 is pressed upward against the action of the spring 66, the groove 68 becomes aligned with the balls 48, 50, 52 allowing the balls to move radially outward. In this situation a fitment 70 on a cap 72 can be placed into the connector 30. When the outer sleeve is released, it is forced downward along the inner sleeve 32 by the spring 66. The lip 64 aligns with the balls 48, 50, 52, forcing the balls radially inwardly to engage the fitment 70. Downward motion of the outer sleeve 34 is limited by the split ring 60. Ridges 69 on the outside of the outer sleeve 34 can provide a better grip for manipulating the outer sleeve 34. The fitment 70 comprises a cylindrical stem 74 with a circumferential groove 76 for engaging the balls 48, 50, 52.

The cap 72 is generally circular and, like the base, has a concave surface 78 which is tightened against the patella. In addition, one or more pins may be provided on the concave surface 78 to more securely grip the patella and prevent any motion of the patella relative to the clamp.

An adjustable scale 80 is also attached to the cap 72. Two arms 82, 84 extend radially outward from an edge 86 of the cap 72. Between the two arms 82, 84 is placed a sliding scale 88 which has adjustment tab 90 on one end and a feeler 92 on the other. The sliding scale 88 is retained between the arms 82, 84 with a end cap 94 which may be attached to the arms 82, 84 by screws (not shown) or other fasteners. A scale lock 96 is provided to hold the scale 80 in a selected position. The scale lock 96 comprises a bolt 98 with a lever 100 for tightening. The scale lock 96 can be screwed through a threaded bore in one of the arms 82 to press the scale 88 against the other arm 84 and thereby secure the scale. The use of the scale 88 will be more fully explained below.

Underneath the bracket 12 is a T-shaped guide plate 102. A central stem 104 of the guide plate 102 has a bore 106. A bolt 108 on a handle 110 passes through the bore 106 and into a threaded bore 112 in the bracket 12. By turning the handle 110, the guide plate 102 can be tightened against the bracket 12 and held in a selected position. If the handle is loosened, the guide plate can swing around the base 14. This permits a surgeon to select a appropriate angle for sawing a patella and also permits the surgeon to use the clamp and saw guide on either right or left knee of a patient.

Two arms 114, 116 extend on either side of the central stem 104. Each arm 114, 116 supports a guide pin 118, 120, respectively. A saw block 122 is mounted on the guide plate 102. The guide pins 118, 120 slide in guide holes 124, 126, respectively, in the saw block 122. A slot 128 in the saw block 122 receives a sagittal blade and holds the saw blade in a plane perpendicular to an axis through the bolt 20 and the handle 110. A lower edge 130 of the slot 128 is extended so that the feeler 92 on the scale 88 can rest against it. This permits a measurement to be made from an upper side 132 of the cap 72 to the lower edge 130 of the slots 128. Markings on the scale 88 are calibrated so that the measurement read on the scale gives the distance from the top of a patella held against the concave surface 78 of the cap to the bottom edge of the intended cut. In practice, the desired depth of cut would be set on the scale and the scale locked in position with the scale lock. Then saw block would be advanced against the scale. Before a cut would be made, the scale would be moved.

The saw block 122 is advanced using a jack screw 134 which passes through a threaded bore 136 in the guide plate 102. The jack screw comprises a knob 138 and a bolt 140. A collar 142 is also attached to the bolt 140. The collar 142 comprises a upper disk 144 and a lower disk 146 separated by a spacer 148. The upper disk 144 and the spacer 148 engage a T-shaped slot 150 in the saw block. The lower disk 146 presses against an under side 152 of the saw block. A relief bore 154 in the guide plate permits the saw block 122 to be set flush against guide plate. By turning the jack screw 134 the axial displacement of the saw block with respect to the clamp can be adjusted. When the displacement has been established by the surgeon, the scale 88 can be moved and the blade of the sagittal saw can be passed through slot 128. The surgeon can then remove a precisely determined amount of the patella and produce a surface which is both flat and in an appropriate plane with respect to the remaining patella for receiving a patellar prosthesis.

After the flat surface is cut onto the patella, it may be necessary or advisable to use additional or specialized caps with the patellar clamp 10. Theses caps can be held temporarily in a storage apparatus located at a bottom end 156 of the handle 110. The caps should have fitments like fitment 70 described above in connection with the cap 72. The storage apparatus comprises an elastomeric cored plug 158 adapted to be inserted in a bore in the bottom end of the handle 110. The cored plug 158 has a central core 160 for receiving a fitment 70. A circumferential groove 162 is provided for receiving a elastic o-ring 164. Three equally spaced radial through bores 166, 168, 170 are provided for receiving balls 172, 174 and 176 respectively. On each of the bores 166, 168, 170, an inner lip 178 is provided to prevent the balls from being forced into the core 160. Because of the elastic nature of the o-ring 164, a fitment 70 on the cap 72 can be snapped in the storage apparatus for temporary storage.

Our invention may be embodied in other specific forms without departing from the spirit or essential characteristics thereof. The scope of our invention is to be defined by the appended claims, and not by the foregoing description, and all changes which come within the meaning of equivalency of the claims are intended to be encompassed therein.

We claim as our invention:

1. A surgical apparatus for holding a patella for resection and for providing a sagittal saw guide, said apparatus comprising
    a base for supporting said patella, a cap opposed to said base for pressing said patella against said base, means for clamping said patella between said base and said cap, a sagittal saw guide adapted to be axially displaced along an axis through said base and said cap, pivoting means pivotal about said axis for supporting said saw guide, and means for securing said pivoting means at a selected angular displacement.

2. The surgical apparatus according to claim 1 further comprising means for measuring an axial amount of bone to be resected from said patella.

3. The surgical apparatus according to claim 2 wherein the measuring means comprise a scale adjustably mounted on said cap.

4. The surgical apparatus according to claim 3 wherein the measuring means further comprise feeler means attached to said scale for engaging the saw guide.

5. The surgical apparatus according to claim 4 wherein the saw guide comprises a slot for receiving a sagittal saw, said slot having an upper side and a lower side and wherein the feeler is adapted to encounter the lower side of said slot.

6. The surgical apparatus according to claim 1 further comprising means for mounting said cap on and removing said cap from said clamping means.

7. The surgical apparatus according to claim 6 wherein the cap comprises fitment means and wherein the mounting and removing means comprise an inner sleeve for receiving said fitment means, said inner sleeve having at least one radially directed bore, means slidingly disposed in said radially directed bore for gripping said fitment means, and an outer sleeve surrounding said inner sleeve for selectively forcing said gripping means radially inward against said fitment means.

8. The surgical apparatus according to claim 7 wherein said at least one radially directed bore comprises a plurality of radially directed bores equally spaced from each other around said inner sleeve.

9. The surgical apparatus according to claim 8 wherein the gripping means comprise spheres.

10. The surgical apparatus according to claim 6 further comprising means for storing said cap when said cap is not held by said mounting and removing means.

11. The surgical apparatus according to claim 10 wherein said cap comprises a fitment means and wherein said storage means comprise a sleeve having an exterior surface and a central bore for receiving said fitment means, a circumferential external groove on said exterior surface of said sleeve, at least one through bore extending from said external groove to said central bore, means slidingly received in said through bore for gripping said fitment means, and spring means for forcing said gripping means towards said central bore to engage said fitment means whenever said fitment means are inserted in said central bore.

12. The surgical apparatus according to claim 11 wherein the spring means comprise an elastomeric o-ring.

* * * * *